United States Patent [19]

Irick, Jr. et al.

[11] 4,159,985

[45] Jul. 3, 1979

[54] HETEROCYCLIC PHENYL ESTER ULTRAVIOLET STABILIZERS

[75] Inventors: Gether Irick, Jr.; Charles A. Kelly, both of Kingsport, Tenn.

[73] Assignee: Eastman Kodak Company, Rochester, N.Y.

[21] Appl. No.: 765,509

[22] Filed: Feb. 1, 1977

Related U.S. Application Data

[62] Division of Ser. No. 484,844, Jul. 1, 1974, Pat. No. 4,020,080.

[51] Int. Cl.$^2$ .............................................. C07D 285/12
[52] U.S. Cl. ........................ 260/302 D; 260/306.8 D
[58] Field of Search ................... 260/302 D, 306.8 D

[56] References Cited

U.S. PATENT DOCUMENTS 4,020,080  4/1977  Irick et al. ...................... 260/302 D Primary Examiner—Alton D. Rollins
Attorney, Agent, or Firm—Clyde L. Tootle; Daniel B. Reece, III

[57] ABSTRACT

The invention relates to heterocyclic phenyl ester compounds which have been found to be effective ultraviolet stabilizers. The invention also relates to ultraviolet degradable organic compositions containing an amount of a heterocyclic phenyl ester composition to prevent such degradation. These stabilizers are effective in the presence of other additives commonly employed in polymeric compositions including, for example, pigments, colorants, fillers, reinforcing agents and the like. These ultraviolet stabilizers may be incorporated into the organic compositions such as polymers by adding to the polymer melt or dissolved in the polymer dope, coated on the exterior of the shaped or molded article, film or extruded fiber.

11 Claims, No Drawings

HETEROCYCLIC PHENYL ESTER ULTRAVIOLET STABILIZERS

This is a division of application Ser. No. 484,844 filed July 1, 1974, now U.S. Pat. No. 4,020,080.

This invention relates to heterocyclic phenyl ester ultraviolet stabilizers and their use in organic compositions. More particularly, the invention relates to heterocyclic phenyl ester compositions and the stabilization of ultraviolet degradable organic compositions against deterioration resulting from the exposure to such radiations with heterocyclic phenyl ester compositions.

The degradative effects of ultraviolet light on various organic compositions is well known in the art. The photo-deterioration or degradation is of particular concern with organic photo-degradable compositions which are exposed to ultraviolet light, such as sunlight, for long periods of time. One group of such photo-degradable organic compositions is polymeric compositions such as polyolefins, polyesters and the like. On exposure to sunlight for extended periods of time, these polymeric compositions degrade and their physical properties are reduced to render the polymeric composition less useful for most applications. Therefore, considerable effort has been directed to providing a solution to the photo-degradation problem of polymeric compositions. As a result of this effort, there have been discovered many additives and stabilizers which improve the stability of polymeric compositions.

Moreover, various additives and stabilizers exhibit the power to absorb electromagnetic radiation within the band of 2900 to 4000 A. and, when incorporated in various plastic materials such as transparent sheets, the resultant sheet acts as a filter for all the radiation passing through and will transmit only such radiations as are not absorbed by the sheet and/or the absorbing agent. It is thus possible to screen out undesirable radiations and utilize the resulting transparent sheet as a filter in many technical and commercial applications, such as wrappings for food products and the like.

While there are many additives, stabilizers and mixtures thereof which are known in the art to improve the ultraviolet light stability of organic compositions, there is a need in the art for more efficient and effective stabilizers to prevent the photo-degradation of organic compositions susceptible to photo-degradation. Therefore, to provide a more effective and efficient ultraviolet stabilizer for organic compositions susceptible to such degradation would be an advance in the state of the art.

It is, therefore, an object of the present invention to provide more effective and efficient ultraviolet light stabilizer compositions.

Another object of the present invention is to provide useful compositions characterized by improved resistance to ultraviolet degradation and deterioration.

It is still another object of the present invention to provide compositions containing heterocyclic phenyl ester compositions which are resistant to ultraviolet degradation.

It is a still further object of this invention to provide processes for improving the resistance of organic materials to deterioration and degradation by actinic radiation and especially ultraviolet radiation.

It is a still further object of this invention to provide compositions and processes for improving the resistance of organic materials to deterioration and degradation by actinic radiations including short wave-length visible radiations.

Further objects and advantages of the invention will be apparent to those skilled in the art from the accompanying disclosure and claims.

In accordance with the present invention, organic compositions are provided which are useful as ultraviolet stabilizers. These organic compositions contain a heterocyclic phenyl ester group connected through a carboxyl group to an aromatic ring which, upon exposure to ultraviolet light, may undergo the "photo-Fries" rearrangement. The organic compositions of the present invention are heterocyclic phenyl esters having the following structure:

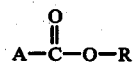

wherein
A is a member of the group comprising members having the structure

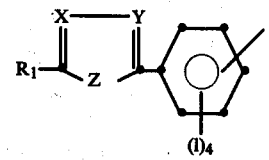

wherein
X and Y are a carbon atom or a nitrogen atom;
Z is an oxygen atom, a sulfur atom, a nitrogen atom, or a nitrogen atom containing a hydrogen atom or a substituted or unsubstituted lower alkyl group having 1 to 12 carbon atoms;
$R_1$ is hydrogen, chloro, bromo, lower alkyl, substituted lower alkyl, cycloalkyl, substituted cycloalkyl, aryl, substituted aryl, lower alkylaryl, aryl-substituted-aryl, alkoxy, substituted amino and cyano.
I is the same as $R_1$ and is present on all positions of the benzenoid ring, except the carbon atom attached to the Y substituent and the carbon atom attached to the carboxyl group connecting the heterocyclic aromatic A group with the aromatic B group, said carboxyl connecting group is attached to the benzenoid ring in either the meta or para position from the carbon atom connected to the Y substituent; and
B is an aryl group having the formula

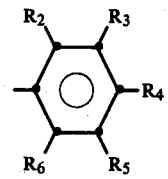

wherein
$R_2$, $R_3$, $R_4$, $R_5$ and $R_6$ are hydrogen, lower alkyl, substituted lower alkyl, cycloalkyl, substituted cycloalkyl, aryl, substituted aryl, lower alkylaryl, aryl-substituted-aryl, alkoxy, hydroxy, substituted amino, carboalkoxy, nitrile, chloro, bromo and the substituents $R_2$ and $R_3$, $R_3$ and $R_4$, $R_4$ and $R_5$, and $R_5$ and $R_6$, combined with the carbon atoms to which they are attached, are joined alkylene groups completing a carbocyclic ring which can be substituted with any of the substituents listed above for $R_2$, $R_3$, $R_4$, $R_5$ and $R_6$. It is necessary that at least one of $R_2$ or $R_6$ be hydrogen, so that on exposure to ultraviolet light, the heterocyclic phenyl ester composition should be capable by the "photo-Fries" rearrangement of forming a phenol group in that position formerly joined through an oxygen atom to the carbonyl linking group. The remaining $R_2$, $R_3$, $R_4$, $R_5$ and $R_6$ can all be one of the substituents listed above or different listed substituents.

Lower alkyl in this application means substituted or unsubstituted, branched or unbranched alkyl groups containing 1 to 12 carbon atoms. Substituted means having thereon any of the substituents listed above for $R_2$. The "alk" of the alkoxy or carboalkoxy means an alkyl group of 1 to 20 carbon atoms. Substituted aryl and cycloalkyl means substituted by any of the substituents listed for $R_1$.

Suitable A groups are, for example, moieties having the formula:

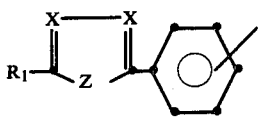

and include substituted and unsubstituted 2-oxadiazolylphenyl, 2-thiazolylphenyl, 2-triazolylphenyl, 2-oxazolylphenyl, and 2-imidazolylphenyl and the like.

Examples of suitable 2-oxadiazolylphenyl moieties are those having the formula:

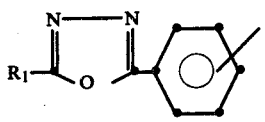

such as 5-(4-chlorophenyl)-1,3,4-oxadiazol-2-yl, 5-phenyl-1,3,4-oxadiazol-2-yl, 5-methylsulfonyl-1,3,4-oxadiazol-2-yl, 5-(2,4-dichlorophenyl)-1,3,4-oxadiazol-2-yl, 5-methyl-1,34,-oxadiazol-2-yl, 5-(4-phenyl)phenyl-1,3,4-oxadiazol-2-yl, 5-cyano-1,3,4-oxadiazol-2-yl, 5-(4-cyanophenyl)-1,3,4-oxadiazol-2-yl, and 5-(4-methoxyphenyl)-1,3,4-oxadiazol-2-yl, and the like.

Examples of suitable 2-thiadiazolylphenyl moieties are those having the formula:

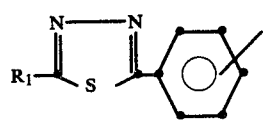

such as 5-phenyl-1,3,4-thiadiazol-2-yl, 5-(4-chlorophenyl)-1,3,4-thiadiazol-2-yl, 5-methylsulfonyl-1,3,4-thiadiazol-2-yl, 5-ethoxy-1,3,4-thiadiazol-2-yl, 5-phenyl-1,3,4-thiadiazol-2-yl, 4-(4-phenyl)phenyl-1,3,4-thiadiazol-2-yl, 4-cyclohexyl-1,3,4-thiadiazol-2-yl, 5-(3-methoxyphenyl)-1,3,4-thiadiazol-2-yl, and 5-cyano-1,3,4-thiadiazol-2-yl, and the like.

Examples of suitable 2-triazolylphenyl moieties are those having the formula:

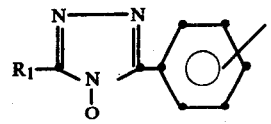

wherein Q is hydrogen or a substituted or unsubstituted lower alkyl group containing 1 to 12 carbon atoms, such as 5-phenyl-1,3,4-triazol-2-yl, 5-(4-cyanophenyl)-1,3,4-triazol-2-yl, 5-cyano-1,3,4-triazol-2-yl, 4-(4-methoxyphenyl)-1,3,4-triazol-2-yl, 1-(n-butyl)-5-(2,4-dichlorophenyl)-1,3,4-triazol-2-yl, 1,3,4-triazol-2-yl, 5-phenyl-1,3,4-triazol-2-yl, 5-methylsulfonyl-1,3,4-triazol-2-yl, 1-methyl-5-phenyl-1,3,4-triazol-2-yl, and the like.

Examples of suitable 2-oxazolylphenyl moieties are those having the formula:

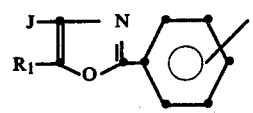

wherein J is the same as $R_1$, such as 5-phenyl-2-oxazolyl, 4,5-diphenyl-2-oxazolyl, 4,5-dimethyl-2-oxazolyl, 4-chloro-5-cyano-2-oxazolyl, 4-phenyl-5-cyano-2-oxazolyl, 5-methylsulfonyl-2-oxazolyl, 5-cyclohexyl-2-oxazolyl, 4,5-dichloro-2-oxazolyl, 5-ethoxy-2-oxazolyl, and the like.

Examples of suitable 2-thiazolylphenyl moieties are those having the formula:

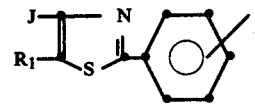

wherein J is the same as $R_1$, such as 4-phenyl-5-chloro-2-thiazolyl, 4,5-dichloro-2-thiazolyl, 4-chloro-5-cyano-2-thiazolyl, 4-ethoxy-5-phenyl-2-thiazolyl, 4,5-dimethyl-2-thiazolyl, 4,5-dicyano-2-thiazolyl, 5-phenyl-2-thiazolyl, and the like.

Examples of suitable 2-imidazolylphenyl moieties are those having the formula:

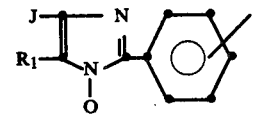

wherein J is the same as $R_1$ and Q is hydrogen or a substituted or unsubstituted lower alkyl group having 1 to 12 carbon atoms, such as 1-methyl-4,5-diphenyl-2-imidazolyl, 4-chloro-5-cyano-2-imidazolyl, 5-phenyl-2-imidazolyl, 1-ethyl-5-phenyl-2-imidazolyl, 4,5-diphenyl-2-imidazolyl, 1-benzyl-4-phenyl-5-cyano-2-imidazolyl, 1-methyl-4-cyano-2-imidazolyl, 4-methoxy-5-phenyl-2-imidazolyl, 4,5-dichloro-1-benzyl-2-imidazolyl, and the like.

Suitable B groups having the formula:

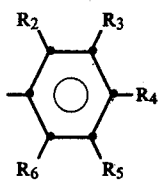

are 2,4-dimethoxyphenyl 3-methoxyphenyl, 3-methylphenyl, 3,5-dimethylphenyl, 3,5-dimethoxyphenyl, 4-octylphenyl, 4-dodecylphenyl, 3-octylphenyl, 2,4-dichlorophenyl, 4-methoxyphenyl, 2,4-di-t-butylphenyl, 3(2-ethylhexyloxy)phenyl, 3-dodecyloxyphenyl, 4-cyanophenyl, 4-bromophenyl, 3-hydroxyphenyl, 3-cyclohexylphenyl, 3,4,5-trimethylphenyl, 3-phenoxyphenyl, 3-acetamidophenyl and 4-acetamidophenyl.

The heterocyclic esters can be prepared by reacting the acid chloride with a phenol. For example, one group of organic compounds useful as ultraviolet stabilizers is, for example, oxadiazolylbenzoate compositions having the formula

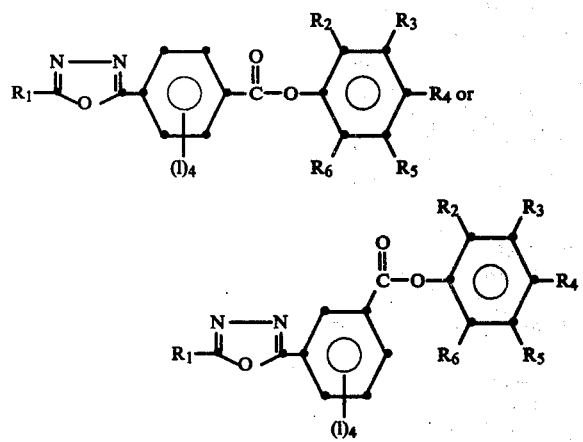

One method for preparing these benzoxazole compounds is illustrated by the following procedure:

(meta or para)

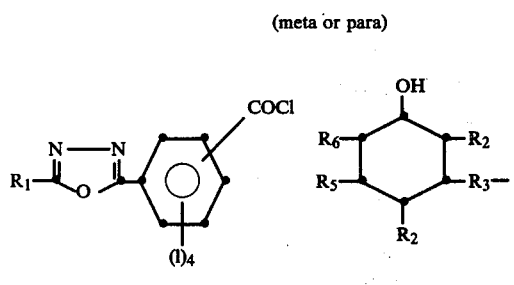

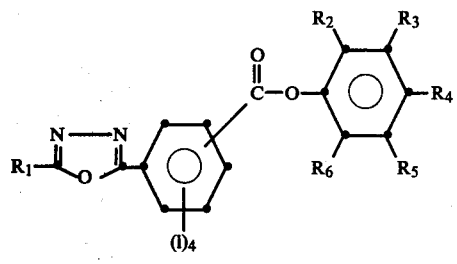

III

Substituents $R_1$ through $R_6$ and (I) are defined hereinabove. It is necessary that at least one of $R_2$ or $R_6$ be hydrogen so that, on exposure to ultraviolet light, the aryl ester of the heterocyclic aromatic is capable by the "photo-Fries" rearrangement of forming a phenol group in that position formerly joined through an oxygen atom to the carbonyl linking group, as for example

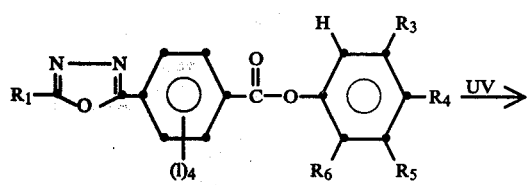

III

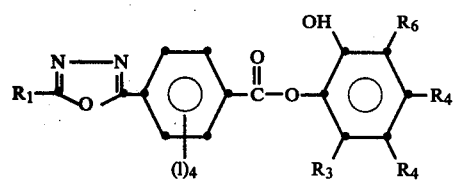

IV

The acid chlorides (I) were prepared by reaction of the corresponding acid [See Zh. Obshch. Khim., 38, 100 1-5 (1968); Chem. Abstr. 69, 96568 (1968)] with freshly distilled thionyl chloride [See J. Chem. Soc. 101, 2476 (1912)]. The phenols were obtained from commercial sources, or were prepared by standard methods; a critical requirement is that one of the positions adjacent to the phenolic hydroxyl group be unsubstituted. It is believed that the "photo-Fries" rearrangement can occur upon ultraviolet exposure of the esters III and that these rearrangement products IV are effective stabilizers.

The heterocyclic phenyl ester compositions can be added to organic compositions which are susceptible to ultraviolet degradation. Such compositions include, for example, polymeric compositions such as polyester fiber and moldable compositions, such as poly(ethylene terephthalate), poly(tetramethylene terephthalate) and the like; unsaturated polyesters; polyolefins such as, for example, high, medium and low density polyethylene, polypropylene, polybutene and the like; polyamides such as nylon 6, nylon 66 and the like; polycarbonates; poly(vinyl chloride); cellulose esters; cellulose ethers;

acrylic/butadiene/styrene plastic; acrylics such as poly(methyl methacrylate); polystyrene; and gelatin. Such compositions also include natural and synthetic rubbers such as polybutadiene, and unsaturated organic compositions such as oils and the like, as well as compositions containing such organic compositions.

The heterocyclic phenyl ester compositions as effective ultraviolet stabilizers or screening agents are generally used in an amount of from 0.01 to 10%, by weight, based on the weight of the organic material to which they are added. While a detectable amount of ultraviolet screening and stabilization may be obtained with amounts less than 0.01%, this amount of stabilization or screening would be of little practical utility in a commercial application. Moreover, while amounts greater than 10%, by weight, provide effective ultraviolet stability and screening, such concentrations are undesirable because of cost and the deleterious effect which such concentrations may have on the mechanical properties of the organic composition in which the stabilizer is incorporated. Preferably, the stabilizer is used in an amount of from about 0.1 to about 5% by weight. For example, an amount of 2%, by weight, of the stabilizer effectively stabilizes cellulose butyrate plastic compositions.

The ultraviolet stabilized organic compositions of the present invention may also contain other additives, pigments, colorants, stabilizers and the like. For example, polymeric compositions, such as polyolefins, may also contain and generally do contain other additives such as white or colored pigments or colorants, antioxidants, plasticizers, flow aids, processing aids, polymeric modifiers and the like.

These heterocyclic phenyl ester ultraviolet stabilizers may be incorporated into organic compositions by melt-blending or may be added onto the surface of an organic plastic material prior to being molded into a suitable object, or added to the surface of the molded object. These materials can also be added to coatings and the like which can be applied to the surface of a molded object.

This invention will be further illustrated by the following examples, although it will be understood that these examples are included merely for purposes of illustration and are not intended to limit the scope of the invention.

EXAMPLE 1

3-Methoxyphenyl 4-(5-phenyl-1,3,4-oxadiazol-2-yl)benzoate can be prepared by the following procedure:

To a solution of 4.0 g. (0.1 mole) sodium hydroxide in 200 ml. water was added 12.4 g. (0.1 mole) 3-methoxyphenol. The mixture was stirred for 10 min. and 200 ml. of chloroform was added, followed by the dropwise addition of a solution of 28.4 g. (0.1 mole) 4-(5-phenyl-1,3,4-oxadiazol-2-yl)benzoyl chloride in 500 ml. chloroform. The mixture was refluxed for 3 hours after the addition was complete. The reaction mixture was then cooled to 30° C. and the chloroform layer separated and washed with water until neutral. The solvent was removed by distillation, the residue trituarated with chilled isopropyl alcohol and crude product collected by filtration. The off-white solid was recrystallized from methyl cellosolve/isopropyl alcohol to give 21 g. nearly colorless product.

EXAMPLE 2

2,4-Di-tert-butylphenyl, 3-(5-cyclohexyl)-1,3,4-oxadiazol-2-yl)benzoate can be similarly prepared by the procedure of Example 1 as follows:

20.6 2,4-di-tert-butylphenol (0.1 mole) was added to a solution of 4.0 g. (0.1 mole) sodium hydroxide in 200 ml. water. A solution of 29.1 g. 3-(5-cyclohexyl-1,3,4-oxadiazol-2-yl)benzoyl chloride was added and refluxing was continued for 3 hours. On workup, 24 g. colorless solid was obtained.

Other oxadiazolylbenzoate esters can be prepared by substituting other 1,3,4-oxadiazol-2-ylbenzoyl chlorides such as 4-[5-(4-phenyl-phenyl)-1,3,4-oxadiazol-2-yl]benzoyl chloride, 4-(5-chloro-1,3,4-oxadiazol-2-yl)-2-chlorobenzoyl chloride, 4-(5-methyl-1,3,4-oxadiazol-2-yl)benzoyl chloride, 4-(5-methoxy-1,3,4-oxadiazol-2-yl)benzoyl chloride, 4-(5-cyano-1,3,4-oxadiazol-2-yl)-2,5-dibromobenzoyl chloride, 4-[5-(4-methylphenyl)-1,3,4-oxadiazol-2-yl)benzoyl chloride, 4-(5-phenoxy-1,3,4-oxadiazol-2-yl)benzoyl chloride, 3-(5-phenyl-1,3,4-oxadiazol-2-yl)benzoyl chloride, 3-(5-cyclohexyl-1,3,4-oxadiazol-2-yl)-4-chlorobenzoyl chloride, 3-(5-n-butyl-1,3,4-oxadiazol-2-yl)benzoyl chloride, 3-(5-methyl-1,3,4-oxadiazol-2-yl)benzoyl chloride, 3-(5-bromo-1,3,4-oxadiazol-2-yl)-4-methylbenzoyl chloride or 3-(5-ethoxy-1,3,4-oxadiazol-2-yl)-4-methoxybenzoyl chloride for 4-(5-phenyl-1,3,4-oxadiazol-2-yl)benzoyl chloride.

Also, other oxadiazolylbenzoate esters can be prepared by substituting other phenols, such as 2,4-dimethoxyphenol, 3-methylphenol, 3,4,5-trimethylphenol, 4-octylphenol, 2,4-di-cyclohexylphenol, 4-dodecylphenol, 3-octylphenol, 2,4-dichlorophenol, 3-bromophenol, 4-chlorophenol, 3-phenoxyphenol, 3-dodecyloxyphenol, 3-n-butoxyphenol, 4-cyanophenol, 4-cyclohexylphenol, 4-phenylphenol, resorcinol, 2,4-di-t-butylphenol, 2,4-dimethylphenol, 4-methoxyphenol for 3-methoxyphenol.

EXAMPLE 3

3-Methoxyphenyl, 4-(5-cyclohexyl-1,3,4-thiadiazol-2-yl)benzoate can be prepared by the procedure of Example 1 as follows:

3-Methoxyphenol (12.4 g.) was reacted with 23.3 g. 4-(5-cyclohexyl-1,3,4-thiadiazol-2-yl)benzoyl chloride as in Example 1. Work-up gave 18.0 g. buff-colored solid.

Other thiadiazolyl benzoate esters can be prepared by substituting other 1,3,4-thiadiazol-2-yl-benzoyl chlorides such as 4-(5-phenyl-1,3,4-thiadiazol-2-yl)benzoyl chloride, 4-(5-chloro-1,3,4-thiadiazol-2-yl)benzoyl chloride, 4-(5-ethyl-1,3,4-thiadiazol-2-yl)benzoyl chloride, 4-(5-methoxy-1,3,4-thiadiazol-2-yl)benzoyl chloride, 4-(5-cyano-1,3,4-thiadiazol-2-yl)-2-bromobenzoyl chloride, 4-[5-(4-methoxyphenyl)-1,3,4-thiadiazol-2-yl]benzoyl chloride, 4-(5-phenoxy-1,3,4-thiadiazol-2-yl)benzoyl chloride, 3-(5-phenyl-1,3,4-thiadiazol-2-yl)benzoyl chloride, 3-(5-n-propyl-1,3,4-thiadiazol-2-yl)benzoyl chloride, 3-(5-bromo-1,3,4-thiadiazol-2-yl)-4-chlorobenzoyl chloride or 3-(5-iso-butoxy-1,3,4-thiadiazol-2-yl)-4-ethoxybenzoyl chloride for 4-(5-cyclohexyl-1,3,4-thiadiazol-2-yl)benzoyl chloride.

Also, other thiadiazolylbenzoate esters can be prepared by substituting other phenols, such as those of Example 2, for 3-methoxyphenol.

EXAMPLE 4

3-Methoxyphenyl, 4-(1-methyl-5-phenyl-1,3,4-triazol-2-yl)benzoate can be prepared by the procedure of Example 1 as follows:

3-Methoxyphenol (12.4 g.) was reacted with 29.8 g. 4-(1-methyl-5-phenyl-1,3,4-triazol-2-yl)benzoyl chloride as in Example 1. Work-up gave 22 g. nearly colorless solid.

Other triazolyl benzoate esters can be prepared by substituting other 1,3,4-triazol-2-yl-benzoyl chlorides such as 4-(1-methyl-5-cyano-1,3,4-triazol-2-yl)benzoyl chloride, 4-(1-methyl-5-methylsulfonyl-1,3,4-triazol-2-yl)benzoyl chloride, 4-(1-benzyl-5-chloro-1,3,4-triazol-2-yl)benzoyl chloride, 3-(5-methoxy-1,3,4-triazol-2-yl)benzoyl chloride, 3-[1-ethyl-5-(2,4-dichlorophenyl)-1,3,4-triazol-2-yl]benzoyl chloride, 3-(1-n-dodecyl-5-ethyl-1,3,4-triazol-2-yl)benzoyl chloride for 4-(1-methyl-5-phenyl-1,3,4-triazol-2-yl)benzoyl chloride.

Also, other triazolylbenzoate esters can be prepared by substituting other phenols, such as those of Example 2, for 3-methoxyphenol.

EXAMPLE 5

4-Cyanophenyl, 4-(4,5-diphenyl-2-oxazolyl)benzoate can be prepared by the procedure of Example 1 as follows:

4-Cyanophenol (11.9 g.) was reacted with 36 g. 4-(4,5-diphenyl-2-oxazolyl)benzoyl chloride as in Example 1. Work-up gave 31 g. off-white solid.

Other oxazolyl benzoate esters can be prepared by substituting other oxazolylbenzoyl chlorides such as 4-(4-phenyl-5-cyano-2-oxazolyl)benzoyl chloride, 4-(4,5-dichloro-2-oxazolyl)benzoyl chloride, 4-(4-chloro-5-cyano-2-oxazolyl)benzoyl chloride, 4-(4,5-dimethyl-2-oxazolyl)benzoyl chloride, 4-(4-phenyl-2-oxazolyl)benzoyl chloride, 4-(5-phenyl-2-oxazolyl)benzoyl chloride, 4-(5-acetamido-2-oxazolyl)benzoyl chloride, 3-(4,5-diphenyl-2-oxazolyl)benzoyl chloride, 3-(4,5-dichloro-2-oxazolyl)benzoyl chloride, 3-(4,5-dimethyl-2-oxazolyl)benzoyl chloride or 3-(4-phenyl-5-cyano-2-oxazolyl)benzoyl chloride for 4-(4,5-diphenyl-2-oxazolyl)benzoyl chloride.

Also, other oxazolyl benzoate esters can be prepared by substituting other phenols, such as those of Example 2, for 4-cyanophenol.

EXAMPLE 6

3-Methoxyphenyl, 4-(5-phenyl-2-thiazolyl)benzoate can be prepared by the procedure of Example 1 as follows:

3-methoxyphenol (12.4 g.) was reacted with 30 g. 4-(5-phenyl-2-thiazolyl)benzoyl chloride as in Example 1. Work-up gave 34 g. light tan solid.

Other thiazolyl benzoate esters can be prepared by substituting other thiazolylbenzoyl chlorides such as 4-(4,5-diphenyl-2-thiazolyl)benzoyl chloride, 3-(4,5-diphenyl-2-thiazolyl)benzoyl chloride, 4-(4,5-dimethyl-2-thiazolyl)benzoyl chloride, 3-(4,5-dimethyl-2-thiazolyl)benzoyl chloride, 4-(4-chloro-5-methyl-2-thiazolyl)benzoyl chloride, 3-(5-cyano-2-thiazolyl)benzoyl chloride, 4-(4,5-dichloro-2-thiazolyl)benzoyl chloride or 3-(4-ethyl-5-acetamido-2-thiazolyl)benzoyl chloride for 4-(5-phenyl-2-thiazolyl)benzoyl chloride.

Also, other thiazolyl benzoate esters can be prepared by substituting other phenols, such as those of Example 2 for 3-methoxyphenol.

EXAMPLE 7

3-Ethylphenyl, 4-(1,4,5-trimethyl-2-imidazolyl)benzoate can be prepared by the procedure of Example 1 as follows:

3-Ethylphenol (12.2 g.) was reacted with 24.9 g. 4-(1,4,5-trimethyl-2-imidazolyl)benzoyl chloride as in Example 1. Work-up gave 29.6 g. nearly colorless solid.

Other imidazolyl benzoate esters can be prepared by substituting other imidazolylbenzoyl chlorides such as 4-(4,5-dimethyl-2-imidazolyl)benzoyl chloride, 4-(1-benzyl-4,5-dimethyl-2-imidazolyl)benzoyl chloride, 4-(1-n-butyl-4,5-diphenyl-2-imidazolyl)benzoyl chloride, 4-(1-methyl-4-cyano-5-cyclohexyl-2-imidazolyl)benzoyl chloride, 3-(1,4,5-trimethyl-2-imidazolyl)benzoyl chloride, 3-(1-β-cyanoethyl-4,5-diphenyl-2-imidazolyl)benzoyl chloride or 3-(4-chloro-5-acetamido-2-imidazolyl)benzoyl chloride for 4-(1,4,5-trimethyl-2-imidazolyl)benzoyl chloride.

EXAMPLE 8

The stabilizing effects of the ultraviolet stabilizers of the present invention in polyester plastic are shown in the following table:

| | Typical Weathering Data for Poly(Tetramethylene Terephthalate) Containing 1% of Heterocyclic Phenyl Ester Stabilizers | | |
|---|---|---|---|
| | Flatwise Impact Strength After Exposure to a Mercury Lamp For Hours Indicated | | |
| Additive | 0 | 300 | 500 |
| None | 19 | 6 | 1 |
| 3-Methoxyphenyl 4-(5-phenyl-1,3,4-oxadiazol-2-yl)benzoate | 19 | 19 | 17 |
| 2,4-Di-tert-butylphenyl 3-(5-cyclohexyl-1,3,4-oxadiazol-2-yl)benzoate | 20 | 19 | 18 |
| 4-Cyanophenyl 4-(5-chloro-1,3,4-oxadiazol-2-yl)-2-chlorobenzoate | 18 | 18 | 16 |
| 3,4,5-Trimethylphenyl 4-(5-methyl-1,3,4-oxadiazol-2-yl)benzoate | 19 | 18 | 15 |
| 2,4-Dichlorophenyl 3-(5-cyano-1,3,4-oxadiazol-2-yl)benzoate | 19 | 18 | 18 |
| 3-n-Butoxyphenyl 4-(5-phenyl-1,3,4-thiodiazol-2-yl)benzoate | 19 | 17 | 17 |
| 4-Cyanophenyl 4-(4,5-diphenyl-2-oxazolyl)benzoate | 19 | 17 | 16 |
| 2,4-Di-t-butylphenyl 4-(4-cyano-5-phenyl-2-oxazolyl)benzoate | 20 | 18 | 15 |

-continued
Typical Weathering Data for Poly(Tetramethylene Terephthalate) Containing 1% of Heterocyclic Phenyl Ester Stabilizers

| Additive | Flatwise Impact Strength After Exposure to a Mercury Lamp For Hours Indicated | | |
|---|---|---|---|
| | 0 | 300 | 500 |
| 3-Phenoxyphenyl 4-(4,5-dimethyl-2-oxazolyl)benzoate | 19 | 18 | 14 |
| 2,4-Dimethylphenyl 4-(5-phenyl-2-oxazolyl)benzoate | 18 | 18 | 15 |
| 4-Cyclohexylphenyl 3-(4-chloro-5-cyano-2-oxazolyl)benzoate | 19 | 17 | 16 |
| 4-Bromophenyl 3-(4,5-diphenyl-2-oxazolyl)benzoate | 18 | 16 | 16 |
| 3-Methoxyphenyl 4-(4,5-dimethyl-2-thiazolyl)benzoate | 19 | 17 | 16 |
| 3,5-Dimethoxyphenyl 4-(4-phenyl-5-cyano-2-thiazolyl)benzoate | 18 | 16 | 15 |
| 3,4,5-Trimethylphenyl 4-(5-phenyl-2-thiazolyl)benzoate | 18 | 16 | 16 |
| 2,4-Dichlorophenyl 3-(4,5-dimethyl-2-thiazolyl)benzoate | 19 | 17 | 17 |
| 2,4-Dimethylphenyl 3-(5-acetamido-1,3,4-thiadiazol-2-yl)benzoate | 19 | 17 | 16 |
| 3,5-Dichlorophenyl 3-(5-chloro-1,3,4-thiadiazol-2-yl)benzoate | 19 | 18 | 17 |
| 3-Phenoxyphenyl 4-(5-cyano-1,3,4-thiadiazol-2-yl)benzoate | 20 | 18 | 18 |
| 2,4-Dimethoxyphenyl 4-(1,5-dimethyl-1,3,4-triazol-2-yl)benzoate | 19 | 18 | 17 |
| 3-n-Dodecyloxyphenyl 4-(1-benzyl-5-phenyl-1,3,4-triazol-2-yl)benzoate | 21 | 18 | 18 |
| 4-tert-Octylphenyl 3-(5-cyclohexyl-1,3,4-triazol-2-yl)benzoate | 20 | 17 | 16 |
| 4-Phenylphenyl 3-(5-methoxy-1-n-butyl-1,3,4-triazol-2-yl)benzoate | 17 | 15 | 15 |
| 2,4-Dicyclohexylphenyl 4-[1-ethyl-5-(2,4-dichlorophenyl)-1,3,4-triazol-2-yl]benzoate | 18 | 16 | 15 |
| 4-Cyclohexylphenyl 3-(4,5-diphenyl-2-thiazolyl)benzoate | 19 | 19 | 18 |
| 3-Methoxyphenyl 4-(1,4,5-trimethyl-2-imidazolyl)benzoate | 19 | 17 | 16 |
| 2,4-Dichlorophenyl 4-(1,4-dimethyl-5-phenyl-2-imidazolyl)benzoate | 20 | 16 | 15 |
| 3-Phenoxyphenyl 4-(1-benzyl-4-chloro-5-cyano-2-imidazolyl)benzoate | 19 | 18 | 18 |
| 2,4-Di-tert-butylphenyl 3-(4,5-diphenyl-2-imidazolyl)benzoate | 19 | 17 | 14 |
| 4-Cyanophenyl 3-(4-ethyl-5-chloro-2-imidazolyl)benzoate | 18 | 16 | 14 |
| 4-Bromophenyl 3-(1-n-butyl-4-cyano-5-phenyl-2-imidazolyl)benzoate | 19 | 18 | 17 |

These heterocyclic phenyl ester compositions find particular utility as ultraviolet stabilizers in organic compositions requiring ultraviolet stability. Such compositions include polymeric compositions such as, for example, polyester fiber and molding compositions, poly-o-olefins, polyamides, acrylics, cellulose esters and the like, as well as molded or shaped articles, film and coatings formed from such materials, and the like. Such compositions also include natural and synthetic rubbers, such as natural rubber, as well as organic materials such as oils, fats, and unsaturated organic materials and materials having such materials contained therein such as paints, varnishes, cosmetics and the like. Typical weathering data are shown in Table I.

The invention has been described in detail with particular reference to preferred embodiments thereof, but it will be understood that variations and modifications can be effected within the spirit and scope of the invention.

We claim:
1. A composition of matter having the formula

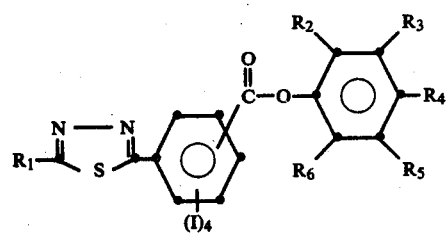

wherein
$R_1$ is hydrogen, chloro, bromo, lower alkyl, chloro substituted lower alkyl, cyclohexyl, phenyl, lower alkylphenyl, phenyl-substituted-phenyl, alkoxy containing 1 to 20 carbon atoms, dimethyl substituted amino, phenyl substituted with not more than two members of the group consisting of chloro, phenyl, cyano, lower alkyl and alkoxy containing 1 to 20 carbon atoms, and cyano;

I is the same as R₁ and is present on all four available positions of the benzenoid ring, the carboxyl connecting group being attached to the benzenoid ring in either the meta or para position from the carbon atom attached to the heterocyclic ring; and at least one of R₂ or R₆ is hydrogen and the other R₂, R₃, R₄, R₅ and R₆ are hydrogen or not more than three members of the group consisting of lower alkyl, cyclohexyl, phenyl, lower alkylphenyl, alkoxy containing 1 to 20 carbon atoms, phenyloxy, hydroxy, nitrile, chloro and bromo.

2. A composition of matter according to claim 1 having the formula:

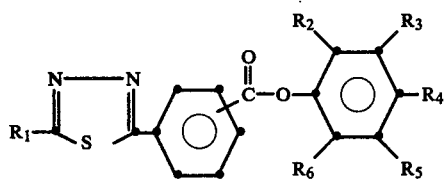

wherein R₁ is hydrogen, chloro, bromo, lower alkyl, chlorine substituted lower alkyl, cyclohexyl, phenyl, alkoxy containing 1 to 20 carbon atoms, cyano, dimethyl substituted amino and phenyl substituted with not more than two members of the group consisting of chloro, phenyl, cyano, lower alkyl and alkoxy containing 1 to 20 carbon atoms; and at least one R₂ or R₆ is hydrogen and the other R₂, R₃, R₄, R₅ and R₆ are hydrogen, or not more than three members of the group consisting of lower alkyl, cyclohexyl, phenyl, phenyloxy, alkoxy containing 1 to 20 carbon atoms, hydroxy, nitrile, chloro, and bromo.

3. A composition of matter according to claim 1 having the formula

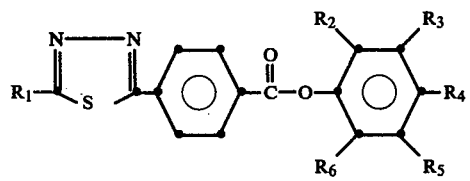

wherein R₁ is hydrogen, lower alkyl, lower alkyl substituted phenyl, or nitrile; and R₂, R₃, R₄ and R₅ are hydrogen, lower alkyl, alkoxy containing 1 to 20 carbon atoms, halogen, cyclohexyl, phenyl, nitrile, and R₆ is hydrogen.

4. A composition of matter according to claim 1 having the formula:

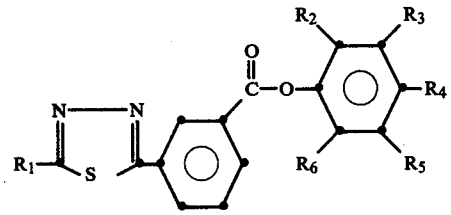

wherein R₁ is hydrogen, lower alkyl, lower alkyl substituted phenyl, or nitrile; and R₂, R₃, R₄ and R₅ are hydrogen, lower alkyl, alkoxy containing 1 to 20 carbon atoms, halogen, cyclohexyl, phenyl, nitrile, and R₆ is hydrogen.

5. A composition of matter according to claim 3 having the formula:

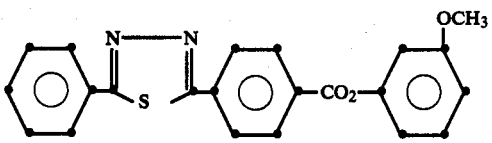

6. A composition of matter according to claim 3 having the formula:

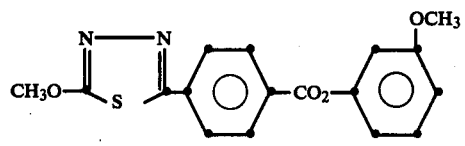

7. A composition of matter according to claim 3 having the formula:

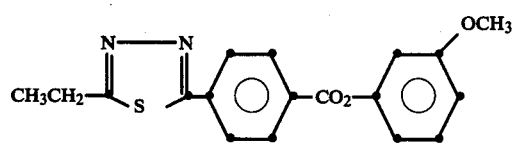

8. A composition of matter according to claim 3 having the formula:

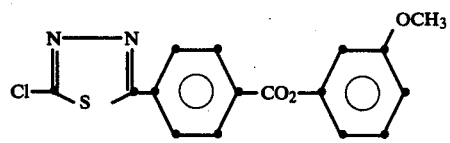

9. A composition of matter according to claim 3 having the formula:

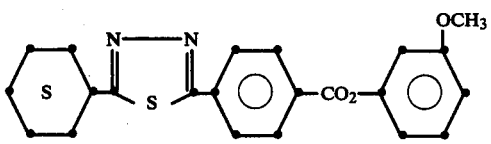

10. A composition of matter according to claim 3 having the formula:

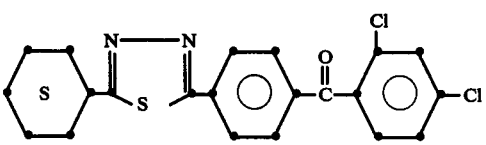

11. A composition of matter according to claim 3 having the formula:

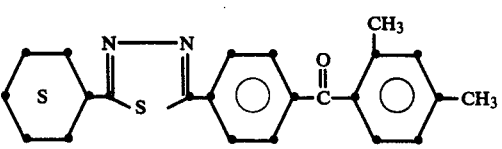

* * * * *